United States Patent

Risteli et al.

[11] Patent Number: 5,342,756
[45] Date of Patent: Aug. 30, 1994

[54] TYPE III COLLAGEN DEGRADATION ASSAY

[75] Inventors: Juha Risteli; Leila Risteli, both of Oulu, Finland

[73] Assignee: Orion-Yhtyma Oy, Turku, Finland

[21] Appl. No.: 435,369

[22] PCT Filed: May 2, 1988

[86] PCT No.: PCT/FI88/00066
§ 371 Date: Dec. 5, 1989
§ 102(e) Date: Dec. 5, 1989

[87] PCT Pub. No.: WO88/08980
PCT Pub. Date: Nov. 17, 1988

[30] Foreign Application Priority Data

May 8, 1987 [GB] United Kingdom ............... 8710925

[51] Int. Cl.$^5$ .............. C12Q 1/00; G01N 33/53; G01N 33/566; G01N 33/551; G01N 33/543; G01N 33/541; A61K 35/14; A61K 37/04; C07K 3/00; C07K 13/00; C07K 15/00; C07K 17/00

[52] U.S. Cl. .................. 435/7.21; 435/7.1; 435/7.2; 435/7.92; 435/7.93; 435/7.94; 435/7.95; 436/501; 436/524; 436/811; 436/578; 436/540; 530/388.2

[58] Field of Search ............ 435/7.93, 7.1, 7.2, 435/7.21, 7.92, 7.94, 7.95; 436/811, 518, 540, 501, 524; 530/380.25

[56] References Cited

U.S. PATENT DOCUMENTS 4,628,027  12/1986  Gay ........................... 435/7

FOREIGN PATENT DOCUMENTS 04104  5/1983  World Int. Prop. O. .

OTHER PUBLICATIONS

Chemical Abstracts vol. 106, (1987) Abstract No. 106:115529d, Anal. Biochem. 1986, 158(2), 334–45.
Chemical Abstracts vol. 105, (1986) Abstract No. 95762y, J. Histochem. Cytochem. 1986, 34(8), 1003–11.
Rennard et al. (1980) Enzyme Linked Immunoassay for Connective Tissue Components Anal. Biochem 104:205–214.

Primary Examiner—Esther M. Kepplinger
Assistant Examiner—D. R. Preston
Attorney, Agent, or Firm—Armstrong, Westerman, Hattori, McLeland & Naughton

[57] ABSTRACT

The degradation of type III collagen in the body is quantitatively determined by measuring the concentration of the liberated aminoterminal telopeptide region of the type III collagen molecule in the body fluid by a specific immunological method. This degradation product is resistant to further degradation and can thus be found in body fluids e.g. in serum or urine. For the determination the telopeptide region must be isolated from a human source e.g. from uterine leiomyoma.

7 Claims, No Drawings

TYPE III COLLAGEN DEGRADATION ASSAY

This invention relates to measuring type III collagen degradation.

Type III collagen is found in several types of connective tissue throughout the human body. Its proportion is characteristically high in young tissue, e.g. in the early phases of wound healing or during the initial phase of development of a fibrosis.

It has become evident in recent years that the development of a fibrotic condition in a parenchymal organ, e.g. cirrhosis of the liver, is dependent on both the synthesis and the degradation of connective tissue. Many diseases are associated with an increase in the amount of collagen synthesized, but as long as the degradative mechanisms can compensate for the increased synthesis, no accumulation of collagen takes place.

Several methods have been described in recent years that allow an estimate to be made of the amount of type III collagen synthesized. The degradation of collagen has been assessed by determining urinary hydroxyproline excretion. However, this method is tedious, needs 24 hour urine collection, and is not specific for a particular collagen type. There is a need for a specific method for determining type III collagen degradation.

The present invention provides such a method, which is quick and simple to practise.

It has been found that the aminoterminal non-helical end of the type III collagen molecule, the so-called telopeptide region, which can be assayed by immunological methods, e.g. by a radioimmunoassay, provides significant information on the degradation of type III collagen.

This discovery can be used in any known method of immunoassay using an antibody specific to type III collagen amino-terminal telopeptide. The invention accordingly provides a method for assaying type III collagen degradation products, which comprises contacting a sample which may contain such products with an antibody specific to type III collagen amino-terminal telopeptide and a label under conditions such that the label becomes bound in an amount which depends on the amount of type III collagen degradation products present in said sample and then assaying the bound and/or unbound label as a measure of the type III collagen degradation products present in said sample. Any method of immunoassay can be used, but preferably a heterogenous method involving a phase separation step, such as those known by the initials RIA, ELISA, FIA, TR-FIA, and IRMA.

Preferably the new method is operated as a radioimmunoassay using isolated human aminoterminal type III collagen telopeptide, and an antibody specific to it. The telopeptide is labelled with a radionuclide, preferably iodine 125, using for example the chloramine-T method, the free iodine being separated by a disposable reverse phase cartridge. Other methods of labelling using enzymatic or fluorescent labels, e.g. europium, can also be used.

Type III collagen has usually been isolated from suitable tissues containing it after pepsin treatment of the tissue. Pepsin digests away the cross-linked telopeptide regions and thus brings helical atelo type III collagen into solution. This material cannot be used for the preparation of the telopeptide antibody required for the present invention or for the telopeptide itself. In accordance with a feature of the invention, therefore, highly purified type III collagen, suitable for us in the method of the invention, is made by extracting suitable human tissue, preferably uterine leiomyoma, with a salt (sodium chloride) solution of suitable molarity and pH to produce a solution of type III collagen in its untruncated form, still containing the telopeptide regions. The type III collagen solution is further purified by salt precipitations and chromatographical methods using techniques known to those skilled in the art. The amino-terminal telopeptide is finally isolated after bacterial collagenase degradation of the highly purified type III collagen. The liberated telopeptide is then purified by chromatographic methods preferably using high performance liquid chromatography (HPLC).

The purified human type III collagen thus prepared, or the isolated telopeptide region coupled to a non-related protein e.g. albumin, is then used to produce a specific antibody, e.g. by immunization of a suitable animal using techniques well known in the art, see, for example, "Immunochemistry of the Extracellular matrix", ed Furthymayr, CRC Press, Boca Raton, U.S.A. 1982 and especially the articles by Furthmayr pp 143–178, Linsenmayer et al pp 179–198 and Timpl et al pp 199–235. A highly specific type III collagen telopeptide antibody is best produced by the subcutaneous injection of type III collagen into test animals, rabbits in the case of polyclonal antibodies and mice for monoclonal antibodies, in the presence of a suitable adjuvant.

The immunoassay itself may be carried out in accordance with known techniques which have been described in the literature, e.g. in the book mentioned above. For example, in one method, labelled type III amino-terminal telopeptide and the sample are both contacted with the antibody, the antigen-antibody complex so formed is separated from uncomplexed starting materials and the complexed or the uncomplexed label is assayed. Separation of the antigen-antibody complex may be facilitated by contacting the antigen-antibody complex with a second antibody specific to the first antibody and separating the antigen-antibody-antibody complex from the uncomplexed starting materials.

The immunoassay method of the invention permits the determined of type III collagen degradation products in human serum or other body fluids. The concentration of the telopeptide in normal serum is about 5 micrograms/liter and is raised, e.g. in cirrhotic and cancer patients, who may have as much as a tenfold increase in the concentration of the type III collagen degradation products. The new method is capable of detecting 1 microgram/liter of the telopeptide.

The following Examples illustrate the invention.

EXAMPLE I

Preparation of human type III collagen and its aminoterminal telopeptide

About 500 g of human uterine leiomyoma was homogenized in, and extracted with, 4M NaCl containing 50 mM tris/HCl, and having pH 7.4, containing protease inhibitors (3 milligrams/liter of phenylmethylmethyl-sulfonyl, fluoride, N-ethylamaleimide and p-hydroxymercuribenzoate and 10 mM EDTA) to wash the tissue and remove and 10 mM EDTA) to wash the tissue and remove soluble proteins. The homogenized tissue is then extracted with 1M NaCl containing the same reagents. Part of the type III collagen dissolves, and can be precipitated with 1.7M NaCl. The precipitate so obtained is chromatographed on a DEAE- Sephacel column (2.5×20 cm), equilibrated with 2M urea, and 50 mM Tris/HCl at pH 8.6, containing the above protease inhibitors. Type III collagen is not bound to this column and comes through it when the column is washed with the column buffer. The type III collagen is then separated form other proteins by gel filtration chromatography on a Sephacel S-500 column (2.5×120 cm) equilibrated with 0.2M ammonium bicarbonate. The final separation from the contaminating type I collagen is achieved by denaturing the collagens in 2M quanidine/HCl, 50 mM Tris/HCl at pH 7.2, at 60° C., and then allowing the type III collagen to renature during dialysis as against distilled water. Type III collagen forms a precipitate which is collected by centrifugation.

The aminoterminal telopeptide can then be obtained by digesting the type III collagen (10 mg in 10 ml 0.2M ammonium bicarbonate) with bacterial collagenase (from Cooper Biomedical, grade CLSPA, 200 micrograms, 4 hours at 37° C.). The digest is directly applied to a gel filtration column of Sephacryl S-200 equilibrated with 0.2M ammonium bicarbonate. Final purification is achieved by high performance liquid chromatography applying reverse phase separation in 0.1% trifluoroacetic acid and eluting the bound telopeptide with increasing concentrations of isopropanol.

EXAMPLE 3

Performance of the radioimmunoassay

One microgram of the aminoterminal telopeptide of type III collagen produced as described in Example 1 is labelled with 1 millicurie of iodine-125 using chloramine-T (5 micrograms). The free iodine is removed, after acidifying the solution, with a preparative Sep-Pak$^R$C$_{18}$ cartridge. The labelled peptide is eluted from the cartridge with 50% isopropanol in 0.1M acetic acid.

Antibody binding curves are prepared with 10 picograms of the labelled peptide. The telopeptide concentration in an unknown sample of serum or other body fluid is determined in the following radioimmuno inhibition assay. A standard amount of the antibody is preincubated with the unknown sample overnight at 4° C. 10 picograms of the labelled peptide is added and the mixture is incubated for 6 hours at 4° C. Then an excess of a second antibody i.e. antibody to the first antibody, is added and the antigen bound is the immune complex is separated by centrifugation from the solution. The inhibition activity of the unknown sample is compared with the inhibition activity of standard concentrations of unlabelled type III collagen aminoterminal telopeptide.

The first antibody used in this method is rabbit gamma-globulin produced in known manner by subcutaneous injection of the purified type III collagen into rabbits. The second antibody is similarly produced in known manner.

We claim:

1. A method for quantitatively determining the degradation of mammalian type III collagen, comprising the steps of:

contacting a sample of a body fluid which may contain an amino-terminal telopeptide degradation product with an antibody specific to type III collagen amino-terminal telopeptide and a label, said label being conjugated to either said antibody or to type III collagen amino-terminal telopeptide, under conditions such that said label becomes bound in an amount which depends on the amount of amino-terminal telopeptide degradation product present in said sample;

separating the unbound starting materials; and assaying the bound and/or unbound label as a measure of the degradation of type III collagen in said sample.

2. The method according to claim 1, wherein said label is conjugated to type III collagen amino-terminal telopeptide in said sample and said labelled type III collagen amino-terminal telopeptide are contacted with said antibody;

the antigen-antibody complex so formed is separated from the uncomplexed starting materials; and the complexed or uncomplexed label is assayed.

3. The method according to claim 2, wherein said antigen-antibody complex is contracted with a second antibody specific to the said antibody; and the antigen-antibody-antibody complex so formed is separated from the uncomplexed starting materials.

4. The method according to claim 2 or 3 wherein the label is a radioactive, enzyme or fluorescent label.

5. The method according to claim 3, wherein said antibody or said second antibody is bound to a solid support; and said antigen-antibody or said antigen-antibody-antibody-complex is separated from the medium in which the contact occurs by separating said solid support.

6. The method according to claim 1, wherein said antibody is a polyclonal antibody.

7. The method according to claim 1, wherein said antibody is a monoclonal antibody.

* * * * *